United States Patent
Meoni

(10) Patent No.: US 10,925,982 B2
(45) Date of Patent: Feb. 23, 2021

(54) ASSEMBLY FOR STERILIZING AND DEPYROGENATING CONTAINERS

(71) Applicant: I.M.A. INDUSTRIA MACCHINE AUTOMATICHE S.P.A. IN SIGLA IMA S.P.A., Ozzano Dell'Emilia (IT)

(72) Inventor: Eddi Meoni, Ozzano Dell'Emilia (IT)

(73) Assignee: I.M.A. INDUSTRIA MACCHINE AUTOMATICHE S.P.A IN SIGLA IMA S.P.A., Ozzano Dell'Emilia (IT)

( * ) Notice: Subject to any disclaimer, the term of this patent is extended or adjusted under 35 U.S.C. 154(b) by 163 days.

(21) Appl. No.: 16/076,927

(22) PCT Filed: Feb. 10, 2017

(86) PCT No.: PCT/EP2017/053060
§ 371 (c)(1),
(2) Date: Aug. 9, 2018

(87) PCT Pub. No.: WO2017/137594
PCT Pub. Date: Aug. 17, 2017

(65) Prior Publication Data
US 2019/0060493 A1     Feb. 28, 2019

(30) Foreign Application Priority Data
Feb. 12, 2016  (IT) .................. 102016000014770

(51) Int. Cl.
*A61L 2/06*     (2006.01)
*A61L 2/26*     (2006.01)
(Continued)

(52) U.S. Cl.
CPC .................. *A61L 2/06* (2013.01); *A61L 2/26* (2013.01); *B65B 3/003* (2013.01); *B65B 55/06* (2013.01);
(Continued)

(58) Field of Classification Search
None
See application file for complete search history.

(56) References Cited

U.S. PATENT DOCUMENTS

| 5,022,165 A * | 6/1991 | Beswick ................. B65B 55/10 34/105 |
| 6,383,449 B1 | 5/2002 | Pennekamp et al. |
| 2008/0260609 A1 * | 10/2008 | Bechini ..................... A61L 2/06 422/291 |

FOREIGN PATENT DOCUMENTS

| JP | H02118350 A | 5/1990 |
| WO | 02051450 A1 | 7/2002 |
| WO | 2006075227 A2 | 7/2006 |

OTHER PUBLICATIONS

International Search Report dated May 11, 2017 re: Application No. PCT/EP2017/053060, pp. 1-3, citing: EP 1 841 654 A2, WO 02/051450 A1 and U.S. Pat. No. 6,383,449 B1.
(Continued)

*Primary Examiner* — Jelitza M Perez
(74) *Attorney, Agent, or Firm* — Cantor Colburn LLP

(57) ABSTRACT

An assembly for sterilizing and depyrogenating containers includes a feeding station, a heating station, and a cooling station. The stations are passed through by a conveyor of containers. The cooling station includes a main unit coupled without discontinuities to the heating station and at least one interchangeable air treatment module. The main unit includes at least one inlet aperture connected without interruptions to an air diffuser arranged above at least a portion of the conveyor, and at least one outlet port. Each module has at least one supply hose with shape and dimensions complementary to those of the at least one inlet aperture in order to be detachably coupled thereto, and at least one
(Continued)

suction channel with shape and dimensions complementary to those of the at least one outlet port in order to be detachably coupled thereto.

11 Claims, 6 Drawing Sheets

(51) Int. Cl.
    *B65B 55/06*     (2006.01)
    *B67C 7/00*     (2006.01)
    *B65B 3/00*     (2006.01)

(52) U.S. Cl.
    CPC ......... *B67C 7/0073* (2013.01); *A61L 2202/15* (2013.01); *A61L 2202/23* (2013.01)

(56) References Cited

OTHER PUBLICATIONS

Written Opinion dated May 11, 2017 re: Application No. PCT/EP2017/053060, pp. 1-5, citing: EP 1 841 654 A2 and WO 02/051450 A1.

"Drying and Sterilizing Tunnel HQL Series" Robert Bosch GmbH, Nov. 2003 (Bosch 1), pp. 1-16.
"HQL—Tunnel for Drying. Sterilizing and Depyrogenating", Robert Bosch GmbH, Bosch 2, Jul. 24, 2018, pp. 1-7.
Bausch + Strobel "Work Order", B+S1 , V. 16, pp. 1-48.
Bausch + Strobel"installation report of CSL", Jul. 10, 2014, B+S4, pp. 1-25.
Bausch + Strobel "International Bausch + Strobel Product Life Cycle File", B+S5, pp. 1-2.
Bausch + Strobel "Operating Instructions for Fully Automatic Sterilizing tunnel DHT 3670", B+S6, 2014, pp. 1-20.
Bausch + Strobel "Cooling Zone, Pages of Technical Drawings", B+S3, pp. 1-18.
Bausch + Strobe, Complete Parts List, B+S2, Sep. 17, 2020, pp. 1-3.
EP Notice of Opposition, dated Sep. 30, 2020 re: Application No. Ep 3 414168 81, pp. 1-15.
JP Office Action dated Nov. 24, 2020 re: Application No. 2018-537814, pp. 1-8, citing: U.S. 2008/0260609 A1, JP H 2-118350A and U.S. Pat. No. 5,022,165 A.
Tobias Hoffmann, "Design document withfunctional specification for the sterilizin tunnel DHT 3670", Bausch + Strobel, B+S7, Aug. 8, 2014. pp. 1-24.

\* cited by examiner

ASSEMBLY FOR STERILIZING AND DEPYROGENATING CONTAINERS

TECHNICAL FIELD

The present disclosure relates to an assembly for sterilizing and depyrogenating containers.

Sterilization here means any process designed to ensure an extreme reduction in the microorganisms (up to their total elimination) present in the containers: generally a container is said to be "sterile" if the probability of finding a microorganism is less than one in a million.

Depyrogenation here means the removal of pyrogens from a material, more specifically from injectable pharmaceutical products. In this case the term is extended to the container in which the medicines will be placed. A pyrogen is any substance that can cause fever in a patient: the term therefore specifically includes bacteria (in particular endotoxins and exotoxins).

The containers that will undergo sterilization and depyrogenation treatment inside the assembly according to the disclosure will preferably be bottles, test tubes, syringes, carpules, phials, jars and the like. The possibility is not ruled out however of using the assembly according to the disclosure for the sterilization and depyrogenation (or optionally only for one of the two treatments) of containers of other kinds.

BACKGROUND

Conventional sterilization and depyrogenation devices comprise a feeding station (by way of which the containers are introduced on an internal conveyor), a sterilization and/or depyrogenation station (corresponding to the superheating of an internal chamber in which the containers are located) and a cooling station (necessary for reducing the temperature of the containers to ranges that permit the introduction of medicines into them without causing any damage or degradation thereof).

If the operation of a conventional device needs to be interrupted for maintenance, all the containers that have already passed through the sterilization and/or depyrogenation station (more specifically those that are located in the cooling station) may come into contact with external agents (for example if an operator has to intervene on the device by removing the housings and accessing the internal conveyor).

Similarly, even if maintenance is carried out while the device is not in service (and therefore does not contain any containers) it is still necessary to have a step of sterilization of the cooling station in order to prevent the products that exit from the sterilization station from undergoing a subsequent contamination in the cooling station.

The use therefore is known of technical solutions that allow the superheating of the cooling station as well, in order to obtain a self-sterilization thereof.

This implementation architecture is however particularly costly and therefore it is not universally used: in some cases a cheaper device is preferred in which the cooling station cannot be superheated, and in which any maintenance operations require different sterilization protocols from those described (protocols that are more complex than the simple self-sterilization described, but which do not have repercussions on the purchase cost of the device itself).

It is therefore evident that there can be two different implementation solutions of sterilization and depyrogenation devices: a first possible implementation has a cooling station provided with means for its superheating (for use for extraordinary sterilization operations as a consequence of maintenance and the like), and a second possible implementation has a cooling station with no means for its superheating.

These two solutions require producers to provide families of different devices, thus increasing the costs of production and the costs of storing raw materials, semi-finished products, and the finished devices.

SUMMARY

The aim of the present disclosure is to solve the above mentioned drawbacks, by providing an assembly for sterilizing and depyrogenating containers which is versatile.

Within this aim, the disclosure provides an assembly for sterilizing and depyrogenating containers with low costs of storing the raw materials and the semi-finished products necessary for building it, as well as the assemblies proper, and in any case lower than the costs of conventional devices.

The disclosure also provides an assembly for sterilizing and depyrogenating containers with characteristics that are structurally and functionally different with respect to those of conventional devices.

The present disclosure further provides an assembly for sterilizing and depyrogenating containers which is low cost, easily and practically implemented, and safely applied.

This aim and these and other advantages which will become better apparent hereinafter, are achieved by providing an assembly for sterilizing and depyrogenating containers according to claim 1.

BRIEF DESCRIPTION OF THE DRAWINGS

Further characteristics and advantages of the disclosure will become better apparent from the detailed description that follows of preferred, but not exclusive, embodiments of the assembly for sterilizing and depyrogenating containers according to the disclosure, illustrated by way of non-limiting example in the accompanying drawings, wherein.

DETAILED DESCRIPTION OF THE DRAWINGS

Figure 1:
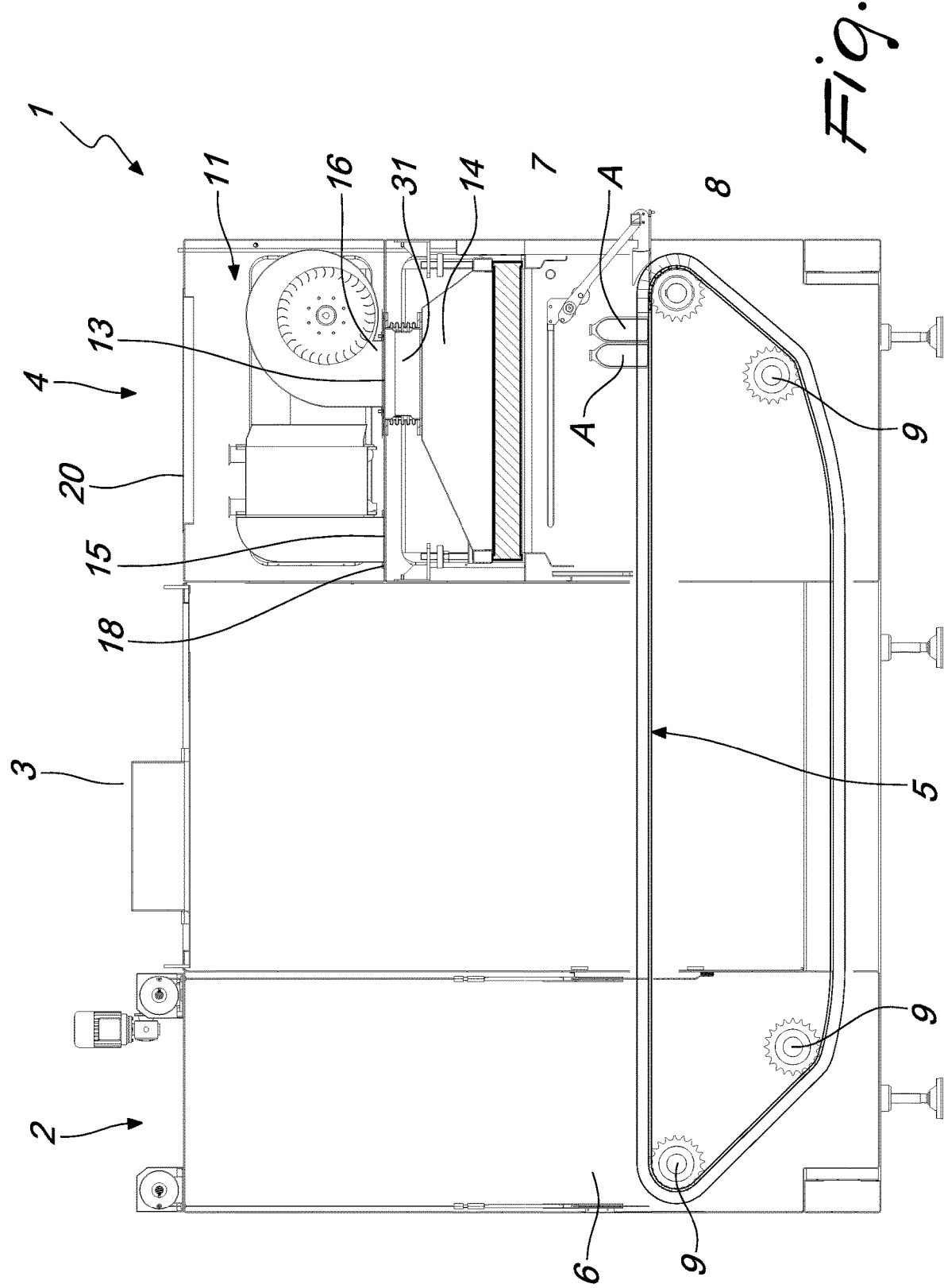
FIG. 1 is a cross-sectional front elevation view, taken along a vertical longitudinal plane, of a possible embodiment of an assembly for sterilizing and depyrogenating containers according to the disclosure.
Figure 2:
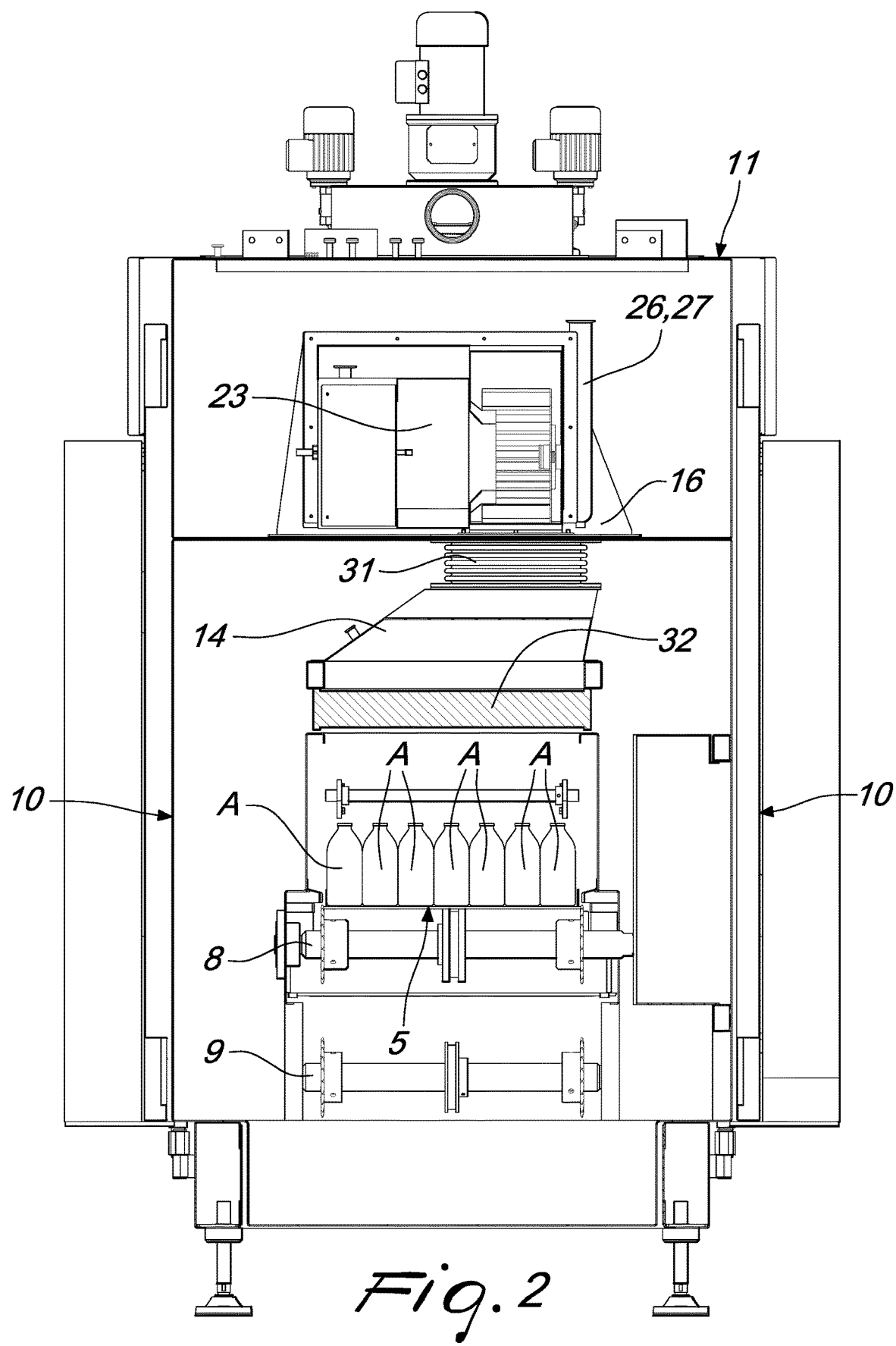
FIG. 2 is a cross-sectional side view, taken along a vertical transverse plane, of the assembly in FIG. 1.
Figure 3:
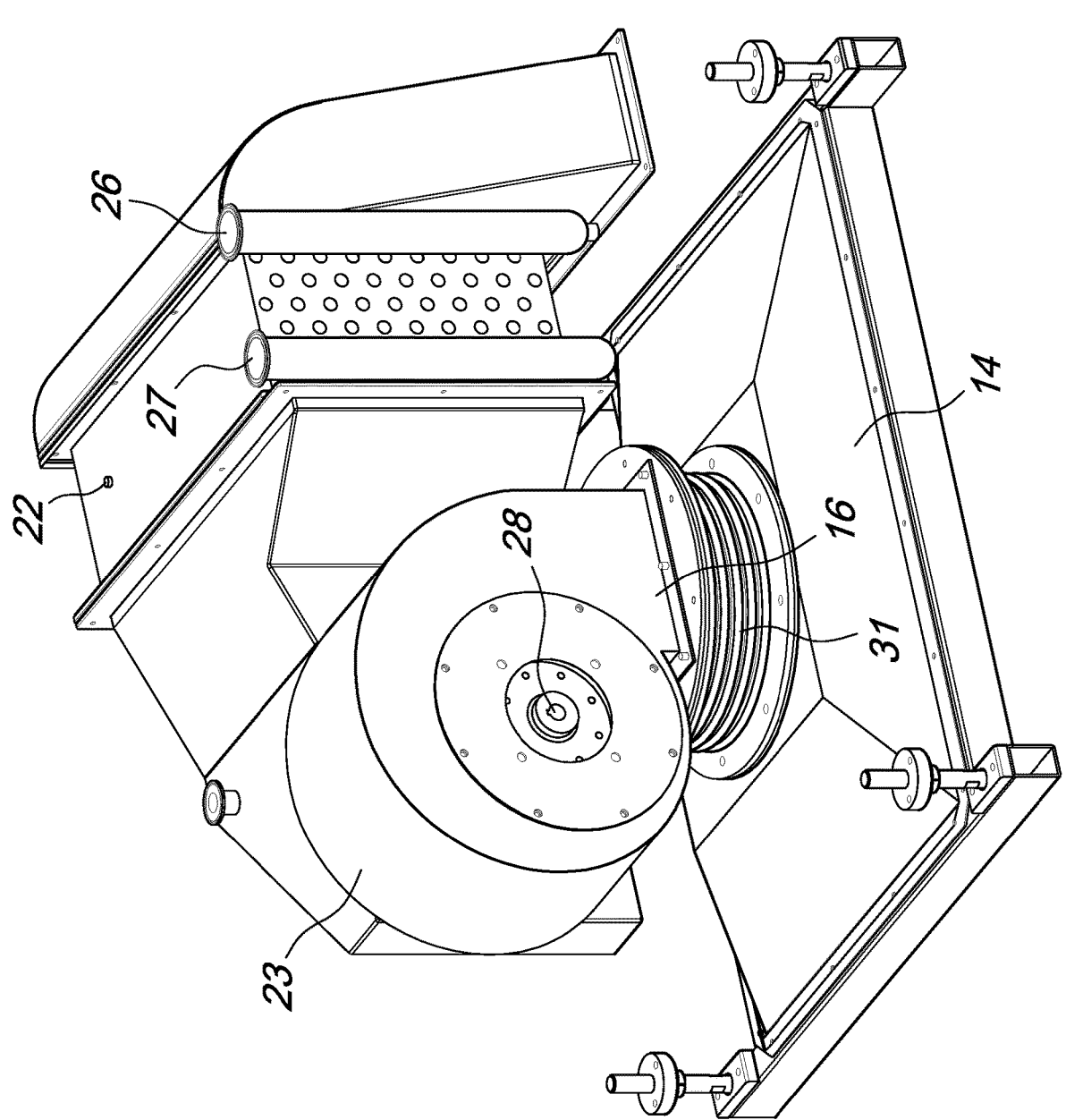
FIG. 3 is a perspective view of the internal part of the air treatment module of the assembly in FIG. 1.
Figure 4:
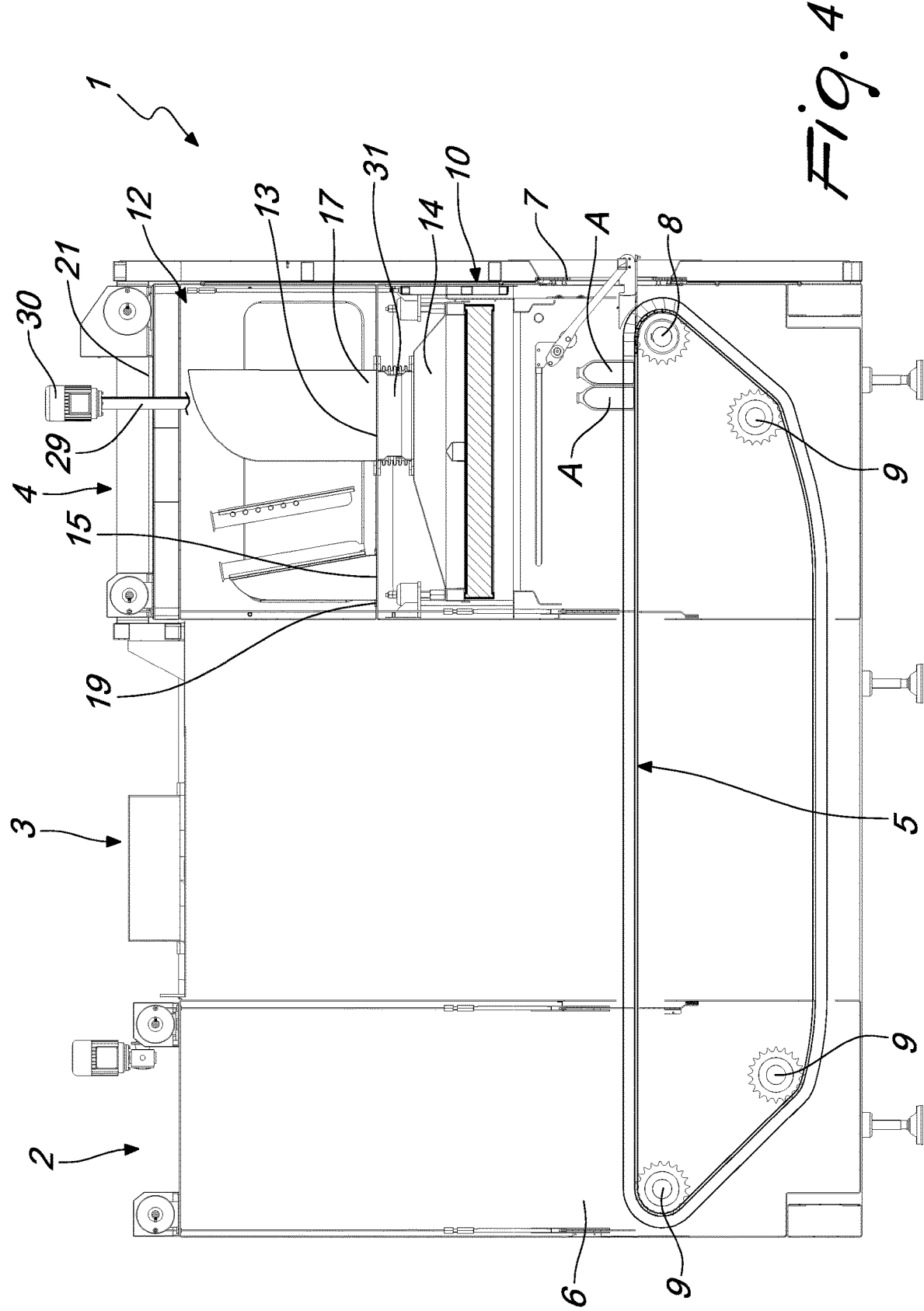
FIG. 4 is a cross-sectional front elevation view, taken along a vertical longitudinal plane, of an alternative embodiment of an assembly for sterilizing and depyrogenating containers according to the disclosure.
Figure 5:
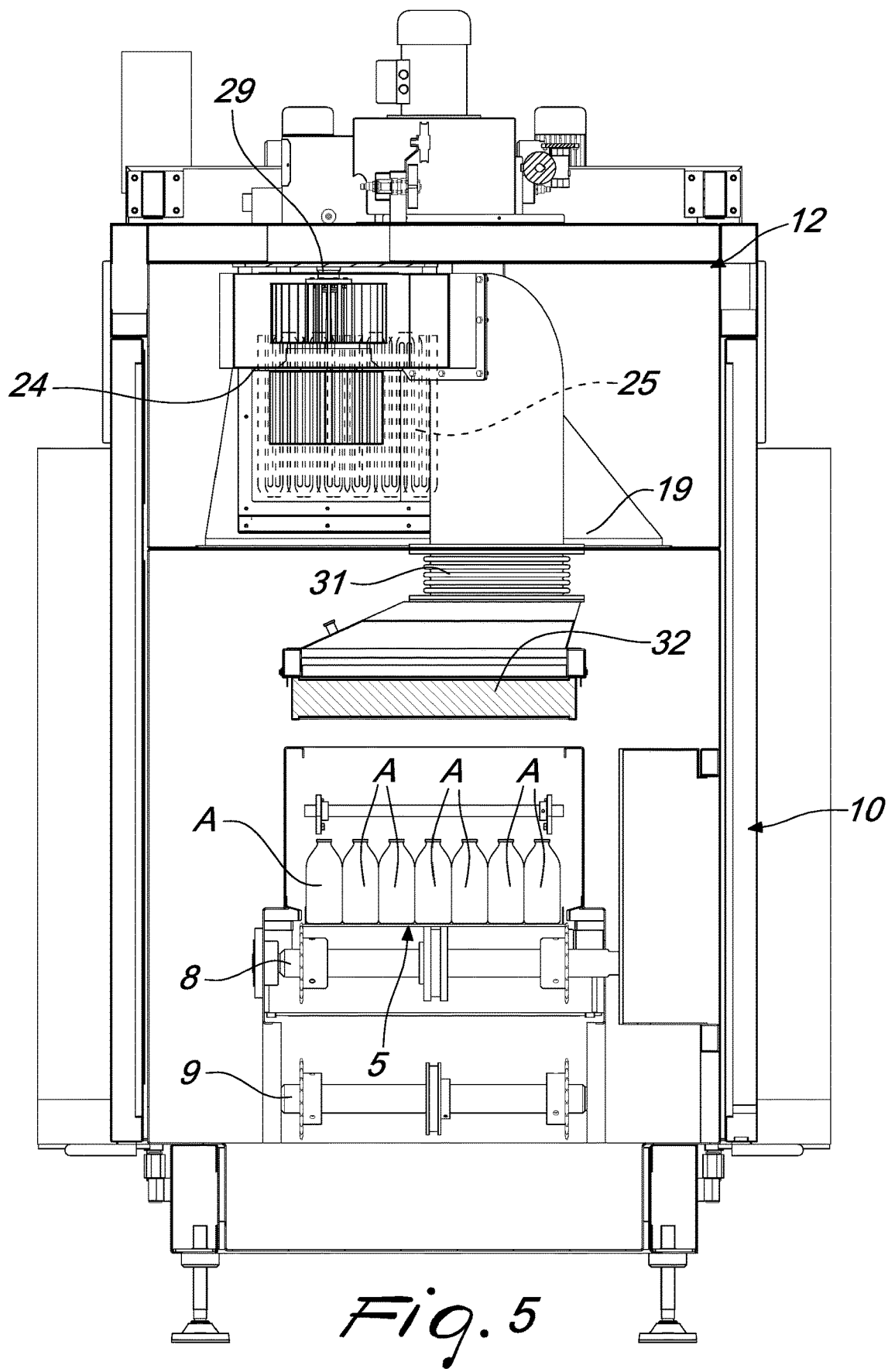
FIG. 5 is a cross-sectional side view, taken along a vertical transverse plane, of the assembly in FIG. 4.
Figure 6:
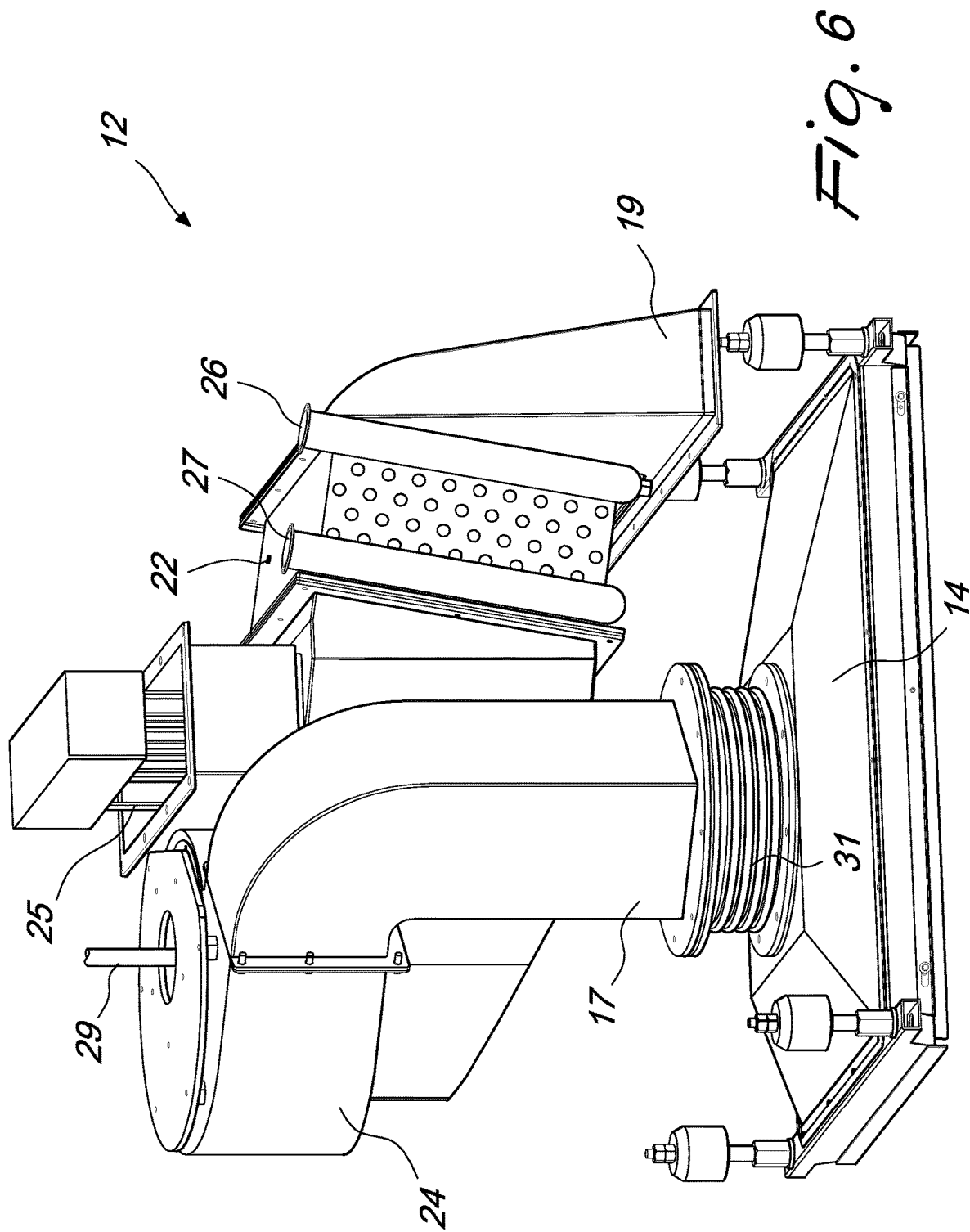
FIG. 6 is a perspective view of the internal part of the air treatment module of the assembly in FIG. 4.

With reference to FIGS. 1-6, the reference numeral 1 generally designates an assembly for sterilizing and depyrogenating containers A.

The assembly 1 according to the disclosure comprises a feeding station 2 (through which the containers A enter the assembly 1 in order to undergo the process of sterilization and depyrogenation), a heating station 3 (inside which the containers A are subjected to high temperatures, thus undergoing the process of sterilization and depyrogenation) and a cooling station 4 (inside which the temperature of the containers A is reduced to a value that makes them suitable for containing a pharmaceutical substance or, in any case, a substance that is thermolabile).

The three stations 2, 3 and 4 listed previously are passed through by a conveyor 5, which is designed to transfer the containers A from an entry opening 6 present in the feeding station 2 to an exit opening 7 present in the cooling station 4.

With reference to the embodiment shown in the accompanying figures, the conveyor 5 can preferably comprise a conveyor belt (in particular of the belt type; the belt can be actuated by way of a specific motorized gearwheel 8 and kept under tension by way of opportune idle gearwheels 9).

According to the disclosure, the cooling station 4 can positively comprise a main unit 10 which is coupled without discontinuities to the heating station 3 and at least one interchangeable air treatment module 11, 12.

The main unit 10 comprises at least one inlet aperture 13, which is connected without interruptions to an air diffuser 14 arranged above at least a portion of the conveyor 5, and at least one outlet port 15.

Each individual module 11, 12 comprises at least one supply hose 16, 17 (in the accompanying figures the supply hose 16 belongs to the module 11 and the supply hose 17 belongs to the module 12), with shape and dimensions complementary to those of the at least one opening 13, for detachable coupling thereto, and at least one suction channel 18, 19 (in the accompanying figures the suction channel 18 belongs to the module 11 and the suction channel 19 belongs to the module 12), with shape and dimensions complementary to those of the at least one outlet port 15, for detachable coupling thereto.

The presence of the supply hoses 16 and 17 and the presence of the suction channels 18 and 19 enable an easy detachable coupling of the respective modules 11 and 12 to the main unit 10.

In practice it is possible to separate a module 11 from the main unit 10 and substitute it with another identical module, or with a different module 12, without having to carry out specific cabling operations, since the shape structure of the modules 11 and 12 is such as to make their juxtaposition with the main unit 10 sufficient.

In other words, the supply hoses 16 and 17 and the suction channels 18 and 19 of the modules 11 and 12 have connection ends arranged in the same positions corresponding to the inlet aperture 13 and to the outlet port 15 of the main unit 10 to which they are respectively to be connected.

With reference to an embodiment of undoubted practical and applicative interest, each module 11, 12 comprises a hollow box-like body 20, 21 which defines an inner air conveyance circuit provided with a suction channel 18, 19, which is outwardly open and can be detachably coupled to a respective outlet port 15 of a main unit 10, and with a supply hose 16, 17, which is outwardly open and can be detachably coupled to an inlet aperture 13 of the main unit 10.

The inner air conveyance circuit of each module 11 and 12 will be intercepted by a radiator 22 and by a fan 23, 24.

With reference to an embodiment that enables the sterilization of the chamber defined inside the main unit 10 (for example following a maintenance intervention), at least one module 12 can conveniently comprise, along its inner air conveyance circuit, at least one heating device 25.

The air, circulating inside the inner air conveyance circuit, flows over the heating device 25 and undergoes an increase in temperature up to a predefined value.

In this manner a high-temperature air flow can exit from the module 12, arrive at the diffuser 14 and strike the chamber defined inside the main unit 10.

With reference to an embodiment that is particularly versatile and efficient, there can be two modules 11 and 12, separate and alternatively coupled to the main unit 10.

A first module 11 comprises an inner air conveyance circuit that is intercepted exclusively by a radiator 22 and by a fan 23.

A second module 12 comprises an inner air conveyance circuit that is intercepted by a radiator 22, by a heating device 25 and by a fan 24.

The simple interchangeability of the two modules 11 and 12 makes it possible to use a device constituted by the feeding station 2, by the heating station 3 and by the main unit 10 as a simple cooling station 4 or as a cooling station 4 adapted to also carry out extraordinary sterilization operations (for example necessary as a consequence of an external maintenance intervention).

In other words, the assembly 1 according to the disclosure comprises an air treatment module 11, 12 chosen (as a function of the operations that need to be carried out on the containers A) from either the first air treatment module 11, which comprises an inner air conveyance circuit intercepted by a radiator 22 and by a fan 23, or the second air treatment module 12, which comprises an inner air conveyance circuit intercepted by a radiator 22, by a heating device 25 and by a fan 24.

It should be noted that the feeding station 2, the heating station 3 and the main unit 10 of the assembly 1 remain the same, whether the first module 11 or the second module 12 is used.

In the context of a more in-depth analysis relating to the implementation aspects of the present disclosure, each module 11 and 12 can profitably comprise an inlet channel 26 and an outlet channel 27 which lead to the radiator 22 for the circulation of a respective cooling fluid.

The cooling fluid can be water (optionally thermostatically-controlled), although the adoption is not ruled out of other cooling fluids optionally originating from a respective cooling assembly.

It should be noted that the heating device 25 can preferably be constituted by a heat exchanger, or an electric resistor in contact with the air in the inner conveyance circuit.

According to a first embodiment, the shaft 28 of the rotor of the fan of the first module 11 is rigidly coupled to the shaft of an electric motor arranged inside the box-like body 20 and connected to a respective electric power supply.

Since the temperature inside the box-like body 20 will in any case be kept below predefined threshold values, insofar as the module 11 only takes care of the cooling of the containers A arranged on the conveyor 5, it will be possible to accommodate the electric motor that actuates the fan 23 inside the box-like body 20 proper, with no risk of overheating the electric motor proper.

In such case the fan 23 will preferably have a horizontal axis (its shaft 28 will have a horizontal axis).

According to a form of execution with operation that is particularly stable and long-lasting over time, the shaft 29 of the rotor of the fan 24 of the second module 12 is rigidly coupled to the shaft of an electric motor 30 arranged outside the box-like body 21 and connected to a respective external electric power supply.

In this case, high temperatures can be achieved inside the box-like body 21 of the module 12 (owing to the heating of the air performed by the heater 25). For this reason, it has been preferred to arrange the electric motor 30, designed to actuate the fan 24, outside the box-like body 21 in order to ensure that the electric motor 30 does not undergo excessive thermal stress.

It is useful to point out that the air diffuser 14 that is arranged above at least a portion of the conveyor 5 is substantially shaped like a hollow prismatic body.

Such a diffuser 14 has an upper base which is open and connected to the inlet aperture 13 of the main unit 10 by way of a respective pipe 31, and a lower base that is also open and facing the conveyor 5.

Such a shape structure makes it possible to regulate the air stream that flows through the diffuser 14 thus making it, substantially, laminar.

It should furthermore be noted that the diffuser 14 comprises, downstream of the upper base and upstream of the lower base, at least one filtering baffle 32 through which the air stream passes during operation.

The filtering baffle 32 (in addition to stopping particles and/or impurities present in the air stream) also contributes to regulating the air flow, reducing its turbulence.

Advantageously the present disclosure solves the above mentioned problems, by providing an assembly 1 for sterilizing and depyrogenating containers which is versatile.

On a single device (constituted by the feeding station 2, by the heating station 3 and by the main unit 10) it is possible to install indifferently an air treatment module 11 that only cools the air stream conveyed by it, or an air treatment module 12 that is also capable of executing, in addition to the cooling of the air stream, a heating thereof which permits extraordinary sterilization operations of the chamber inside the main unit 10.

Positively the assembly 1 according to the disclosure makes it possible to minimize the costs of storing the raw materials and the semi-finished products necessary for building it, as well as the assemblies proper.

In fact it is not necessary to have different components, depending on whether the assembly is intended for sterilization with consequent cooling of the containers A, or there is also the possibility of an extraordinary sterilization of the cooling station 4: in fact it will be sufficient to have a single device (constituted by the feeding station 2, by the heating station 3 and by the main unit 10) on which to install, according to requirements and in an easily interchangeable manner, an air treatment module 11 or an air treatment module 12 (which is also capable of executing extraordinary sterilization operations).

Conveniently the assembly 1 according to the disclosure has different structural and functional characteristics with respect to those of conventional devices, therefore offering the potential user possibilities in terms of versatility and reconfigurability post-installation that have never been possible until now.

Positively the assembly 1 is easily and practically implemented and is low cost: such characteristics make it an innovative technical solution which is safe in use.

The disclosure, thus conceived, is susceptible of numerous modifications and variations. Moreover, all the details may be substituted by other, technically equivalent elements.

In the embodiments illustrated, individual characteristics shown in relation to specific examples may in reality be interchanged with other, different characteristics, existing in other embodiments.

In practice, the materials employed, as well as the dimensions, may be any according to requirements and to the state of the art.

The disclosures in Italian Patent Application No. 102016000014770 (UB2016A000694) from which this application claims priority are incorporated herein by reference.

The invention claimed is:

1. An assembly for sterilizing and depyrogenating containers comprising a feeding station, a heating station, and a cooling station, said stations being passed through by a conveyor of containers, said cooling station comprising a main unit coupled without discontinuities to said heating station and at least one interchangeable air treatment module, wherein said main unit comprises a single inlet aperture which leads, without interruptions, to an air diffuser arranged above at least a portion of said conveyor, and a single outlet port, each said module comprising a single supply hose, with shape and dimensions complementary to those of said single inlet aperture, in order to be detachably coupled thereto, and a single suction channel, with shape and dimensions complementary to those of said single outlet port, in order to be detachably coupled to the same, wherein the single supply hose supplies to the air diffuser only air coming from the single outlet port through the single suction channel and the single outlet port is the only port from which said module is configured to draw air.

2. The assembly according to claim 1, wherein said at least one air treatment module comprises a hollow body that defines an inner air conveyance circuit provided with said single suction channel outwardly open and configured to be detachably coupled to the single outlet port of the main unit, and with said single supply hose outwardly open and configured to be detachably coupled to the single inlet aperture of said main unit, a heat exchanger of the type of a radiator and a fan being installed within the single suction channel.

3. The assembly according to claim 2, wherein said at least one air treatment module comprises an inlet channel and an outlet channel which lead to said radiator for the circulation of a cooling fluid, said inlet and outlet channels being outside the single suction channel.

4. The assembly according to claim 1, wherein one module of said at least one air treatment module comprises an inner air conveyance circuit intercepted by a heating device, air circulating in said inner air conveyance circuit flowing over said heating device and undergoing an increase in temperature up to a predefined value.

5. The assembly according to claim 2, which comprises said at least one air treatment module chosen from either a first air treatment module comprising an inner air conveyance circuit intercepted by a radiator and by a fan, or a second air treatment module comprising an inner air conveyance circuit intercepted by a radiator, by a heating device and by a fan; said first air treatment module and said second air treatment module are separate and configured to be alternatively coupled to said main unit.

6. The assembly according to claim 5, wherein said heating device is an electric resistor.

7. The assembly according to claim 5, wherein the fan of the first air treatment module comprises a rotor with a respective shaft rigidly coupled to a shaft of an electric motor arranged inside the hollow body and connected to a respective electric power supply.

8. The assembly according to claim 5, wherein the fan of the second air treatment module comprises a rotor with a respective shaft rigidly coupled to a shaft of an electric motor arranged outside the hollow body and connected to a respective electric power supply.

9. The assembly according to claim 1, wherein the air diffuser arranged above at least a portion of said conveyor has a hollow prismatic body having an upper base that is open and connected to the single inlet aperture of the main unit by way of a respective pipe, a lower base of said hollow prismatic body being open and facing said conveyor.

10. The assembly according to claim 9, wherein the hollow prismatic body comprises, downstream of the upper base and upstream of the lower base, at least one filtering baffle through which the air stream passes during operation.

11. The assembly according to claim 1, wherein the at least one air treatment module comprises an inner air conveyance circuit formed by the single suction channel and the single supply hose, said inner air conveyance circuit being intercepted by a cooling device and a heating device, both the cooling device and the heating device being installed side by side within the single suction channel.

* * * * *